United States Patent [19]

Wong et al.

[11] Patent Number: 5,284,587
[45] Date of Patent: Feb. 8, 1994

[54] BACTERIA-CONTAINING POLYMER GEL FOR WASTE WATER TREATMENT

[75] Inventors: John M. Wong; Thomas J. Lowe, both of Lakewood; Therese J. Schleiden, Richfield, all of Ohio

[73] Assignee: General Environmental Science, Ohio

[21] Appl. No.: 811,539

[22] Filed: Dec. 20, 1991

[51] Int. Cl.$^5$ .......................... C02F 3/00; C02F 3/02; C12N 11/00; C12N 11/10
[52] U.S. Cl. .................... 210/606; 210/610; 210/611; 210/620; 435/174; 435/175; 435/176; 435/178; 435/182; 435/262.5; 435/288
[58] Field of Search .............. 435/174, 176, 177, 178, 435/180, 182, 262.5, 175, 288; 210/606, 610, 611, 620

[56] References Cited

U.S. PATENT DOCUMENTS

| | | | |
|---|---|---|---|
| 3,767,790 | 10/1973 | Guttag | 435/182 X |
| 3,963,576 | 6/1976 | Horsfall, III et al. | 195/59 |
| 4,321,141 | 3/1982 | Messing | 210/603 |
| 4,416,993 | 11/1983 | McKeown | 435/243 |
| 4,634,672 | 1/1987 | Baumgarten et al. | 435/180 X |
| 4,673,505 | 6/1987 | Wong | 210/611 |
| 4,746,435 | 5/1988 | Onishi et al. | 210/615 |
| 4,810,385 | 3/1989 | Hater et al. | 210/606 |
| 4,882,059 | 11/1989 | Wong et al. | 210/606 |
| 4,885,094 | 12/1989 | Srinivasan et al. | 210/610 |
| 4,925,564 | 5/1990 | Francis | 210/608 |
| 4,929,484 | 5/1990 | Basse | 428/53 |
| 4,940,539 | 7/1990 | Weber | 210/149 |

*Primary Examiner*—David M. Naff
*Attorney, Agent, or Firm*—Birch, Stewart, Kolasch & Birch

[57] ABSTRACT

A bacteria-containing two component polymer gel is provided for solubilizing particulate or colloidal organic materials in wastewater. The gel contains a minor amount of a polymer component that is difficult to solubilize by bacteria in the gel and a major amount of a polymer component that is easier to solubilize by bacteria in the gel. The gel contains bacteria for solubilizing material in wastewater and for solubilizing the gel, and nutrients for the bacteria. The gel also contains a bacteria inhibitor such as sodium sulfide or sodium azide that can diffuse out of the gel at a gel-water interface to allow bacteria to dissolve the gel at the interface while preventing an interior region of the gel from prematurely dissolving. The gel is placed in a housing through which wastewater flows and contacts the gel. The inhibitor diffuses out of the gel at a gel-wastewater interface and bacteria dissolve the gel at the interface to release bacteria that produce extracellular enzymes for dissolving material in the waste water.

16 Claims, 1 Drawing Sheet

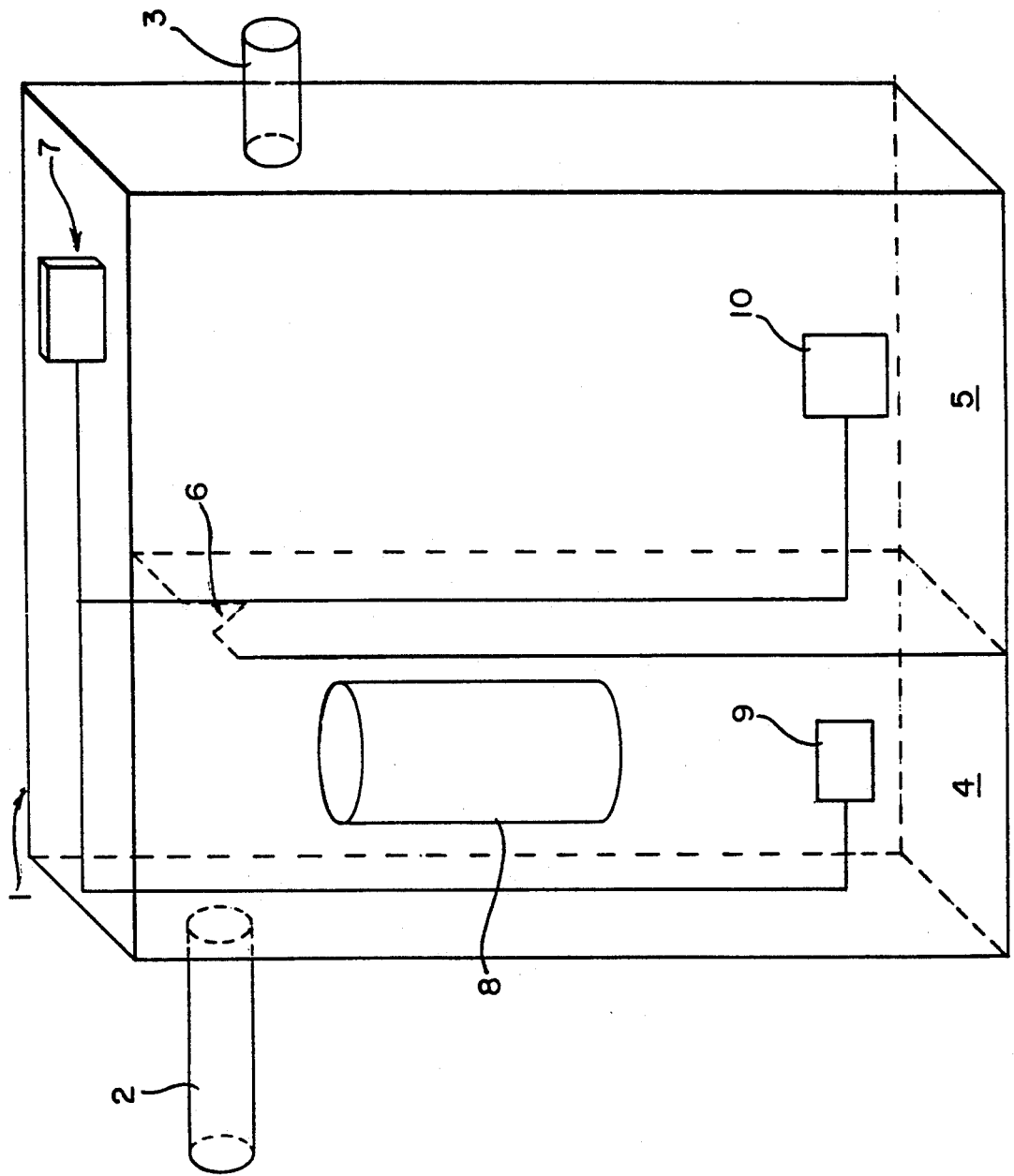

BACTERIA-CONTAINING POLYMER GEL FOR WASTE WATER TREATMENT

BACKGROUND OF THE INVENTION

1. Field of the Invention

The present invention relates to a system and method for enhanced solubilization of particulate and colloidal organic materials in wastewater treatment. The present invention is an effective, convenient system for the preparation and delivery of bacteria and extracellular hydrolytic enzymes used to enhance wastewater treatment. Use of this invention results in increased rates of solubilization of particulate and colloidal organic compounds. This invention is a gel-based, slow release system that can function effectively for 30 days without operator attention.

2. Description of Related Art

A method for preparing aerobic and facultative bacteria such that they produce increased amounts of extracellular enzymes and thereby enhance solubilization of organic compounds in wastewater treatment is disclosed in U.S. Pat. No. 4,882,059. The process (referred to as an activation process) requires either daily operator attention or a high degree of automated process control. There are many wastewater treatment facilities which have a need for enhanced solubilization of organic materials, but cannot effectively employ the method of U.S. Pat. No. 4,882,059.

For example, many villages, trailer parks, apartment complexes, etc., have small wastewater treatment plants (WWTPs) which treat less than 100,000 gallons per day (gpd) of wastewater. Often, these facilities cannot employ more expensive automated process control systems and are staffed for only an hour or so per day such that methods of wastewater treatment requiring additional operator attention cannot be employed. Other examples of less sophisticated wastewater treatment systems include grease traps in restaurants, septic tank systems, and pump stations in the collection systems of WWTPs.

Therefore, it is desired to develop an enhanced wastewater treatment system and method which allows for reduced automated process control and reduced operator attention.

SUMMARY OF THE INVENTION

The present invention relates to a system and method for solubilizing particulate or colloidal materials in waste water treatment. The system includes a bacterial gel system which includes bacteria which can produce extracellular enzymes which solubilize particulate and colloidal organic materials, nutrients which support the growth of said bacteria, at least a gel mass which contains said bacteria and nutrients, and at least a bacterial inhibitor contained in said gel for preventing an interior portion of said gel mass from dissolving; and a housing which provides an aerobic and aqueous environment for said bacterial gel system so as to induce the production of activated bacteria and extracellular enzyme synthesis.

The present invention also encompasses a method for solubilizing particulate or colloidal materials in wastewater treatment which includes the steps of providing bacteria in a bacterial gel system which contains bacteria which can produce extracellular enzymes which solubilize particulate and colloidal organic materials, nutrients which support the growth of said bacteria, at least a gel mass which contains said bacteria and nutrients, and at least a bacterial inhibitor contained in said gel for preventing an interior portion of said gel from dissolving; wherein said bacteria near the surface of said bacterial gel system are released into an aqueous environment under conditions in which said activated bacteria produce increased amounts of extracellular enzymes which solubilize particulate or colloidal materials; and contacting the activated bacteria or the enzymes with the particulate or colloidal materials under conditions which solubilize the particulate or colloidal materials.

The present invention will become more fully understood from the detailed description given hereinbelow and the accompanying drawings which are given by way of illustration only, and thus are not limitative of the present invention.

BRIEF DESCRIPTION OF THE DRAWINGS

The sole FIGURE is a diagrammatic view an embodiment of the automated bacterial injection system of the present invention.

DETAILED DESCRIPTION OF THE INVENTION

In both the system and method of the present invention the following five components are required:

1. Bacteria which can produce extracellular enzymes which hydrolyze (solubilize) particulate and colloidal organic materials.
2. Nutrients which will support the growth of the bacteria incorporated in the system and method of the present invention.
3. A gel which holds the bacteria and nutrients.
4. A bacterial inhibitor which is added to the gel to prevent bacteria from dissolving the gel in the interior gel region.
5. A housing or "Automated Bacterial Injector" (ABI) which provides the aerobic, aqueous environment and the proper hydraulic residence time needed to induce high rate extracellular enzyme synthesis in the bacterial gel system described above.

The extracellular enzyme producing bacteria and nutrients are placed into a gel. The bacteria include at least one species that can solubilize the gel. A bacterial inhibitor, such as sodium sulfide or sodium azide, as disclosed in U.S. Pat. Nos. 3,963,576 and 4,673,505, respectively, which are incorporated herein by reference, is added to the gel to prevent bacteria from rapidly dissolving the gel. The gel is placed into an aerated tank (the ABI). The tank has a water inflow and an equal water outflow. The volume of the tank is typically one to two times that of one day's water flow, providing a one to two day hydraulic residence time in the tank. The bacteria, nutrient, and inhibitor containing gel is placed into this aerating tank. The inhibitor at the gel-water interface diffuses into the water. The bacteria near the water-gel interface are in a region of lessened inhibitor concentration, and these bacteria become active and begin to dissolve the gel. As the gel dissolves, bacteria and nutrients are released into the water, while the interior of the gel remains intact.

A significant aspect associated with the system and method of the present invention is to formulate the bacteria, nutrient, inhibitor and gel base such that once released, the bacteria are subjected to appropriate activation conditions disclosed, for example, in U.S. Pat.

No. 4,882,059, which is incorporated herein by reference, whereby the bacteria produce increased amounts of extracellular enzymes. For example, the bacteria are subjected to conditions such that the level of the nutrient food source drops below 50 mg/l of soluble chemical oxygen demand (sCOD) and the bacteria begin producing increased amounts of enzymes which solubilize particulate or colloidal materials thereby producing activated bacteria. Thereafter, the activated bacteria or enzymes are contacted with the particulate or colloidal materials under conditions which solubilize the particulate or colloidal materials. The amount of soluble food source, nutrients, gel, bacterial inhibitor, cultivation media and bacteria are desirably selected so that the food source is used up by the bacteria in about 8-40 hours, preferably 16-32 hours, most preferably about 24 hours. The soluble chemical oxygen demand (sCOD) of the environment of the bacteria is usually at least about 50 milligrams per liter (mg/l), generally 50 to 1000 mg/l, preferably 100 to 300 mg/l, most preferably about 150 mg/l.

It is also significant to formulate this system such that it takes more than several days for the gel to completely dissolve. The gel must be replaced upon depletion. In order for the system to be useful at wastewater treatment facilities with minimal available manpower, the gel must last at least several days, preferably two to four weeks or longer.

A detailed description of each of the five components employed in the system and method of the present invention is provided below and is followed by a description of several Examples in accordance with the present invention.

A. BACTERIA

1. Functional Requirements

The bacteria employed in the system and method of the present invention must be capable of producing extracellular enzymes. The enzymes produced should be capable of degrading the most common constituents of wastewater: proteins, starches, fats, and cellulose. (Journal Water Pollution Control Federation, Vol. 57, Number 7, pg. 805-816).

2. Characteristics

Many bacteria are known to produce extracellular enzymes Which solubilize these macromolecules. For example, *Bacillus subtillis* is known to produce amylase and protease, (Bacteriological Review, September 1977, Vol. 41, No. 3, pg. 711-753), *Bacillus licheniformis* produces lipase (Journal Applied Bacteriology, Vo. 37, 571-581), while Cellulomonas are commonly known to hydrolyze cellulose.

In the present invention, bacteria and nutrients are immobilized in a gel. In order to provide a time release of these bacteria and nutrients into the aerobic aqueous environment of the ABI (into which the bacteria and nutrient containing gel is placed), it is helpful, but not necessary, to include at least one bacterial species that can solubilize the gel.

In order to provide the greatest practical use, the bacteria included should be non-pathogenic. If the chosen gel requires heating before gel formation, it is most convenient to use bacteria capable of surviving temperatures up to about 80° C., such as sporulated Bacillus.

Bacteria which are most preferred as being useful in fulfilling the above functional and general characteristics are as follows:

a. *Bacillus subtillis*

*Bacillus subtillis* is known to produce amylase and protease. It also produces enzymes which degrade gelatin. *Bacillus subtillis* produces enhanced amounts of these enzymes when subjected to death phase or stationary phase growth conditions.

b. *Bacillus licheniformis*

This bacterium is known to produce lipase in enhanced amounts during stationary and death phase growth conditions.

c. Cellulomonas sp.

Cellulomonas will degrade cellulose, which is well known by those skilled in the art to be a major constituent of wastewater.

d. *Acinetobacter lwoffi*

This bacterium produces enhanced amounts of lipase during stationary and death phase growth conditions.

Each of the above bacteria are non-pathogenic, and produce enhanced amounts of extracellular enzymes during stationary and death phase growth conditions. Collectively, they are effective in speeding the solubilization of the predominant macromolecular constituents of municipal wastewater: starches, proteins, lipids, and cellulose.

B. NUTRIENTS

1. Functional Requirements

The nutrients are considered to be those trapped in the gel matrix as well as the gel itself. The nutrients should provide for rapid growth of the bacteria such that appropriate activation conditions, such as those described in U.S. Pat. No. 4,882,059, can be achieved.

2. Characteristics

The nutrients must provide organic carbon, ammonia or amino acids, orthophosphate, and micronutrients. Commonly used organic carbon sources which promote rapid bacterial growth include yeast extract, peptone, beef extract, tryptone, and carboxylic acids such as acetic acid and citric acid.

The inorganic chemicals could include ammonium chloride, ammonium sulfate, potassium or sodium phosphate, and magnesium sulfate. A non-exhaustive list of preferred nutrients that fulfill the requirements listed above include: yeast extract; sodium acetate; ammonium chloride; potassium phosphate; and magnesium sulfate.

C. GEL FORMULATION

1. Functional Requirements

The purpose of the gel is to immobilize the bacteria and nutrients such that each is slowly released when subjected to the aerobic aqueous environment of the ABI delivery system. The gel must be sufficiently stable so as to provide an appropriate release rate of bacteria and nutrients. Since a purpose of the present invention is to ensure that appropriate activation conditions, such as those disclosed in U.S. Pat. No. 4,882,059, are achieved, the release rate of bacteria and nutrients can be neither too rapid nor too slow.

2. Characteristics

The controlled release of bacteria and nutrients from the gel depends on bacterial hydrolysis of the gel at the gel-water interface, i.e. diffusion of nutrients contained within the gel near the interface into the water, while use of a bacterial inhibitor prevents bacterial hydrolysis of the gel in the interior region of the gel. Therefore, the gel must be firm and stable, yet must be of a chemical composition such that at least one bacterium in the gel will solubilize it.

One way of achieving these requirements is to use a two component gel. A small fraction of the gel can be a polymer that is very difficult to degrade which provides structural integrity to the gel matrix. The majority of the gel can be formed from a substance which is easier to degrade than the polymer.

A non-exhaustive list of gel materials which are difficult to degrade and provide structural integrity include bacterial agar, silica gel, and gellan gum. Non-limiting examples of gel materials which are easier to degrade include gelatin, xanthum gum, and locus bean gum. A suitable gel which may be used in accordance with the present invention is formed using a combination of bacterial agar and gelatin.

D. BACTERIAL INHIBITOR

A key feature of the system and method of the present invention is that the bacterial laden gel will last for a significant period of time before it completely dissolves. While it is useful that bacteria dissolve the gel at the gel-water interface, the interior of the gel mass must not dissolve. In order to prevent premature gel dissolution due to bacterial hydrolysis in the interior gel region, a bacterial inhibitor is added to the gel.

1. Functional Requirements

The bacterial inhibitor must be one that reversibly inhibits bacteria contained in the gel. The inhibitor should be effective above a threshold concentration, below which the bacteria would become active. The inhibitor should be completely water soluble and of sufficiently low molecular weight that it can easily diffuse out of the gel at the gel water interface, rather than be retained by the gel matrix.

2. Characteristics

Two bacterial inhibitors which fit the above requirements are sodium sulfide and sodium azide, as disclosed in U.S. Pat. Nos. 3,963,576 and 4,673,505, respectively. Each can be incorporated into the gel such that the bacteria contained within the gel are prevented from solubilizing the interior region of the gel mass.

One inhibitor which fulfills all the above requirements while not compromising the gel integrity is sodium azide. Sodium azide may be employed in the present invention in accordance with the description of the methods disclosed in U.S. Pat. No. 4,673,505.

E. AUTOMATED BACTERIAL INJECTOR (ABI) HOUSING

The ABI is a housing through which aerated water flows and into which the bacteria and nutrient laden gel is placed. The combination of the ABI housing dimensions, water flow rate, and gel formulation preferably results in attaining appropriate activation conditions, such as those disclosed in U.S. Pat. No. 4,882,059.

1. Functional Requirements

The ABI housing is intended to provide a continuous, flow through an aerobic aqueous environment. The FIGURE illustrates one preferred embodiment of the ABI system in accordance with the present invention. The system includes a housing 1 having a first chamber 4 and a second chamber 5 through which water flows. The water is supplied through an intake conduit 2 and discharged through a discharge conduit 3. The first chamber 4 contains the bacterial and nutrient gel mass 8. If the housing 1 is constructed to hold a six gallon volume, it is preferred that the second chamber 5 be about 50% larger than the first chamber 4, e.g. volumes of 3.6 gal and 2.4 gal, respectively. An air pump or aeration device 7 supplies air through two aquarium style air diffusers 9 and 10 into chambers 4 and 5. A baffle 6 is located between the chambers.

The ABI housing 1 illustrated in the FIGURE has a continuous water feed, and since the ABI chamber has a fixed volume, there is a continuous discharge equal to the influent flow rate. The gel mass s is fully submerged in the water in the first chamber 4. The discharge from the ABI housing contains the bacteria and enzymes produced via appropriate activation conditions as described for example in U.S. Pat. No. 4,882,059, and this discharge flows directly into the wastewater to be treated.

2. Characteristics

The general characteristics of the ABI housing include its volume relative to the water flow rate, its aerobic environment, and the number of chambers in series.

In order to achieve the stationary or death phase growth conditions required to induce high rate extracellular enzyme synthesis, and assuming that the gel is releasing bacteria and nutrients in the proper manner, the ABI housing should provide about 24 to 48 hours of hydraulic retention time in its aerobic chambers. For example, assuming that the influent water flow rate is 6 gallons per day, the volume of the aerobic chambers in the ABI would total 3 to 6 gallons.

Aeration of the ABI housing is necessary to achieve the growth phases desired for enhanced extracellular enzyme production. All that is required is sufficient dissolve oxygen to support the rapid growth of aerobic or facultative bacteria.

A single aerobic chamber suffices to provide the desired ABI conditions. However, single stage reactors are often inefficient in producing bacterial metabolites. Given the same total reaction volume, a plurality of stages will induce higher rate extracellular enzyme production than will a single chamber ABI (J. App. Chem. Biotechnol. 1972, 22, pg 405–416).

For a water influent flow rate of six gallons per day, the ABI should be a two-chambered unit with six gallons of aqueous aerobic reaction volume. The water influent flows directly into the first chamber, and then passes over a baffle into the second chamber. The water would pass through the second chamber and be discharged into the wastewater to be treated. Based on a six gallon per day flow rate, and a combined volume of six gallons in chambers 4 and 5, the total hydraulic retention time would be 24 hours. For a fixed ABI volume, the water flow rate could be cut by one half to 3 gallons per day, and the resulting hydraulic retention time would be 48 hours.

For a given bacterial gel, if the water flow rate is too fast such that stationary or death phase conditions are not achieved, the bacteria will not produce extracellular enzymes at a high rate. As the hydraulic retention time increases, amylase and protease will be the enzymes produced in highest quantity. As the hydraulic residence time is further increased, lipase and cellulase are preferentially produced. The water flow rate can therefore be adjusted for a typical gel formulation to produce relatively large amounts of amylase and protease, or lipase and cellulase.

PREFERRED EMBODIMENTS

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

EXAMPLE I

In order to formulate a preferred embodiment of the invention, the desired bacterial strains are produced, these bacteria are incorporated into the bacterial gel, a nutrient laden but bacterial free gel is prepared, and both nutrient and bacterial gels are then placed into an ABI housing.

Production of Bacterial Suspensions

An Aqueous growth medium was prepared using the following materials:

| Chemical | Concentration (mg/l) |
| --- | --- |
| $NH_4Cl$ | 200 |
| $KH_2PO_4$ | 200 |
| $MgSO_4$ | 50 |
| $CH_3COONa$ | 750 |
| Yeast Extract | 750 |

The above materials were dissolved in 90% deionized water and 10% tap water, and autoclaved at 15 pounds steam for 30 minutes.

Four one liter flasks containing 750 ml each of the above solution were each inoculated with one of the following:
a. *Bacillus subtillis*
b. *Bacillus licheniformis*
c. *Cellulomonas sp.*
d. *Acinetobacter lwoffi*

Using standard sterile procedures, each flask was placed on an orbital shaker at 150 rpm and allowed to grow for 48 hours. At the end of 48 hours, 0.5 grams of sodium azide was added to each flask.

To finish preparing the bacterial gel, 313 ml of deionized water was heated to 80° C. 15 grams of agar was added to this and the mixture was autoclaved at 15 pounds for 15 minutes. 125 ml each of the *Bacillus subtillis* and *licheniformis* suspensions were slowly heated to 80° C. At this time, the Bacillus suspensions were in spore form, and were not damaged by heating. Once the suspensions were at 80° C., 120 grams of gelatin was slowly added with mixing.

Both the Agar containing and the gelatin containing mixtures were cooled to 40° C. Once cooled, both mixtures were combined with 125 ml each of the Cellulomonas and Acinetobacter suspensions. The resulting mixture was poured into a cylindrical mold (3 inch diameter) and allowed to refrigerate at 5° C.

To prepare the nutrient gel, the following technique was performed. 600 ml deionized water, 50 ml tap water, 5 grams of each of $K_2HPO_4$, $MgSO_4$, $NH_4Cl$ and $CH_3COONa$ and 200 grams of yeast extract were combined and heated to 80° C. Once heated to 80° C., 120 grams gelatin and 15 grams agar were added to this with stirring. The mixture was autoclaved at 15 pounds for fifteen minutes, cooled to 40° C., poured into cylindrical molds (3 inch diameter), and refrigerated at 5° C.

Both the bacterial and nutrient gels solidified within 2 hours. The gels were cut into 7 inch lengths, such that each bacterial or nutrient gel was a cylinder with a 3 inch diameter and a 7 inch length. The ABI system requires both a nutrient gel and a bacterial gel. The ABI system functions best when the nutrients are separated from the bacteria, although reduced production of enzymes can be achieved with mixed bacterial/nutrient systems.

The combination of one nutrient gel and one bacterial gel may be referred to as a "GelPac". GelPacs were used in the tests described below in conjunction with ABI units to reduce sludge production in small wastewater treatment plants. Each ABI unit used one GelPac each month.

EXAMPLE II

In order to evidence the efficacy of the ABI system and method of the present invention for reducing sludge, an ABI unit with a 18 gallon capacity similar to the one illustrated in the FIGURE and described above was installed in two of the ten small wastewater treatment plants operated by the Cuyahoga County Sanitary Authority in Cleveland, Ohio. The ten plants range in size from 25,000 to 200,000 gallons per day of wastewater treated. One ABI unit was installed at a plant treating less than 100,000 gallons per day, the other in a plant treating more than 100,000 gallons per day. The remaining eight plants were used as control systems.

The 17 month period of January, 1990 through May, 1991 was used to determine the average amount of sludge produced at the eight control and two test plants. Sludge production was defined to be equal to total pounds of waste activated sludge plus total pounds of effluent suspended solids.

Beginning in June, 1991 and ending six months later through November 1991, a properly sized GelPac was added to each of the two previously installed ABI units on a monthly basis. Operations at the eight control plants were unchanged. The table below summarizes the average sludge production at both the test plants (which employed the ABI units and GelPacs in accordance with the present invention) and control plants during both the baseline (January, 1990–May, 1991) and evaluation (June, 1991–November, 1991) periods:

| Total Sludge Produced = WAS + Effluent SS (All Data in lbs/Month) | | |
| --- | --- | --- |
| | Average Non-treated Plants | Average Treated Plant |
| Baseline | 1134 | 1095 |
| Evaluation | 1110 | 731 |

Sludge production at the untreated plants was essentially unchanged during the evaluation period compared to the baseline period. The GelPac treated system showed a 35% decrease in total sludge production during the evaluation period compared to the baseline.

The above tests exemplify the sludge reduction results achieved using the ABI system and method of the present invention at small wastewater treatment plants. Many other uses of the present invention are also possible and include, for example:
1. reducing solids content in agricultural lagoons;
2. digestion of grease in grease traps;
3. removal of grease from the interior of pipes; and
4. other applications in wastewater treatment where the solubilization of particulate and colloidal material is required.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A solubilizing system for producing activated bacteria and enzymes for solubilizing particulate or colloidal materials in wastewater treatment, comprising:
    a bacteria-containing two component polymer gel including a minor amount of a polymer component that is difficult to solubilize by bacteria in the gel and which component provides structural integrity to the gel and a major amount of a polymer component that is easier to solubilize by bacteria in the gel, said gel containing
    bacteria which can produce extracellular enzymes which solubilize particulate and colloidal organic materials,
    at least one bacteria which solubilizes the gel,
    nutrients which support the growth of said bacteria, and
    a water soluble reversible bacteria inhibitor of sufficiently low molecular weight that it can easily diffuse out of the gel at a gel-water interface while preventing an interior region of said gel from prematurely dissolving; and
    a housing which provides an aerobic and aqueous environment for said bacteria-containing gel so as to induce production and release of activated bacteria and extracellular enzymes for solubilizing particulate and colloidal materials in wastewater.

2. The solubilizing system of claim 1, wherein said bacteria are selected from the group consisting of *Bacillus subtillis, Bacillus licheniformis,* Celulomonas sp. and *Acinetobacter lwoffi.*

3. The solubilizing system of claim 1, wherein the nutrients are selected from the group consisting of yeast extract, peptone, beef extract, tryptone, acetic acid, citric acid, sodium acetate, ammonium chloride, potassium phosphate, magnesium sulfate and combinations thereof.

4. The solubilizing system of claim 1, where said bacteria inhibitor is sodium sulfide or sodium azide.

5. The solubilizing system of claim 1, wherein said housing comprises a plurality of chambers at least one of which contains said bacteria-containing gel, an intake conduit for supplying water to said chambers, a discharge conduit for discharging water containing activated bacteria and enzymes produced by said bacteria-containing gel from said chambers, and an aeration device for supplying oxygen to said chambers.

6. A method for solubilizing particulate or colloidal materials in wastewater treatment, comprising the steps of:
    providing a bacteria-containing two component polymer gel including a minor amount of a polymer component that is difficult to solubilize by bacteria in the gel and which component provides structural integrity to the gel and a major amount of a polymer component that is easier to solubilize by bacteria in the gel, said gel containing
    bacteria which can produce extracellular enzymes which solubilize particulate and colloidal organic materials.
    at least one bacteria which solubilizes the gel, nutrients which support the growth of said bacteria, and
    a water soluble reversible bacteria inhibitor of sufficiently low molecular weight that it can easily diffuse out of the gel at a gel-water interface to allow the bacteria to dissolve the gel at the gel-water interface while preventing an interior region of said gel from prematurely dissolving; and
    contacting said gel with wastewater containing said particulate or colloidal materials whereby bacteria in the gel solubilize said gel to release activated bacteria and extracellular enzymes which solubilize said particulate or colloidal material.

7. The method of claim 6, wherein said bacteria are selected from the group consisting of *Bacillus subtillis, Bacillus licheniformis,* Celulomonas s. and *Acinetobacter lwoffi.*

8. The method of claim 6, wherein the nutrients are selected from the group consisting of yeast extract, peptone, beef extract, tryptone, acetic acid, citric acid, sodium acetate, ammonium chloride, potassium phosphate, magnesium sulfate and combinations thereof.

9. The method of claim 6, wherein said bacteria inhibitor is sodium sulfide or sodium azide.

10. The method of claim 6, wherein said bacteria-containing gel is contained in a housing which comprises a plurality of chambers at least one of which contains said bacteria containing gel, an intake conduit for supplying water to said chambers, a discharge conduit for discharging water containing activated bacteria and enzymes produced by said bacteria-containing gel from said chambers and an aeration device for supplying oxygen to said chambers.

11. The solubilizing system of claim 2, wherein said bacteria inhibitor is sodium sulfide or sodium azide.

12. The method of claim 7, wherein said bacteria inhibitor is sodium sulfide or sodium azide.

13. A solubilizing system for producing activated bacteria and enzymes for solubilizing particulate or colloidal materials in wastewater treatment, comprising:
    a bacteria-containing two component polymer gel including a minor amount of a polymer component that is difficult to solubilize by bacteria in the gel and which component provides structural integrity to the gel and a major amount of a polymer component that is easier to solubilize by bacteria in the gel, said gel containing
    bacteria which can produce extracellular enzymes which solubilize particulate and colloidal organic materials,
    at least one bacteria which solubilizes the gel, nutrients which support the growth of said bacteria, and
    a water soluble reversible bacteria inhibitor of sufficiently low molecular weight that it can easily diffuse out of the gel at a gel-water interface to allow the bacteria to dissolve the gel at the gel-water interface while preventing an interior region of said gel from prematurely dissolving;

a housing which provides an aerobic and aqueous environment for said bacteria-containing gel so as to induce production and release of activated bacteria and extracellular enzymes for solubilizing particulate and colloidal materials in wastewater;

wherein said bacteria are selected from the group consisting of *Bacillus subtillis*, *Bacillus licheniformis*, Celulomonas sp. and *Acinetobacter lwoffie;* wherein the nutrients are selected from the group consisting of yeast extract, peptone, beef extract, tryptone, acetic acid, citric acid, sodium acetate, ammonium chloride, potassium phosphate, magnesium sulfate and combinations thereof; and wherein said bacteria inhibitor is sodium sulfide or sodium azide.

14. The solubilizing system of claim 13, wherein said housing comprises a plurality of chambers at least one which contains said bacteria-containing gel, an intake conduit for supplying water to said chambers, discharge conduit for discharging water containing activated bacteria and enzymes produced by said bacteria-containing gel from said chambers, and an aeration device for supplying oxygen to said chambers.

15. A method for solubilizing particulate or colloidal materials in wastewater treatment, comprising the steps of:

providing a bacteria-containing two component polymer gel including a minor amount of a polymer component that is difficult to solubilize by bacteria in the gel and which component provides structural integrity to the gel and a major amount of a polymer component that is easier to solubilize by bacteria in the gel, said gel containing bacteria which can produce extracellular enzymes which solubilize particulate and colloidal organic materials, at least one bacteria which solubilizes the gel, nutrients which support the growth of said bacteria, and a water soluble reversible bacteria inhibitor of sufficiently low molecular weight that it can easily diffuse out of the gel at a gel-water interface to allow the bacteria to dissolve the gel at the gel-water interface while preventing an interior region of said gel from prematurely dissolving; and contacting said gel with wastewater containing said particulate or colloidal materials whereby bacteria in the gel solubilize said gel to release activated bacteria and extracellular enzymes which solubilize said particulate or colloidal material, wherein said bacteria are selected from the group consisting of *Bacillus subtillis*, *Bacillus licheniformis*, Celulomonas sp. and *Acinetobacter lwoffie;* wherein the nutrients are selected from the group consisting of yeast extract, peptone, beef extract, tryptone, acetic acid, citric acid, sodium acetate, ammonium chloride, potassium phosphate, magnesium sulfate and combinations thereof; and wherein said bacteria inhibitor is sodium sulfide or sodium azide.

16. The method of claim 15, wherein said housing comprises a plurality of chambers as least one of which contains said bacteria-containing gel, an intake conduit for supplying water to said chambers, a discharge conduit for discharging water containing activated bacteria and enzymes produced by said bacteria-containing gel from said chambers, and an aeration device for supplying oxygen to said chambers.

* * * * *